(12) United States Patent
Read

(10) Patent No.: US 7,845,207 B2
(45) Date of Patent: Dec. 7, 2010

(54) TEST APPARATUS AND METHOD OF TESTING

(75) Inventor: Simon Read, Derby (GB)

(73) Assignee: Rolls-Royce, PLC, London (GB)

( * ) Notice: Subject to any disclaimer, the term of this patent is extended or adjusted under 35 U.S.C. 154(b) by 21 days.

(21) Appl. No.: 12/292,108

(22) Filed: Nov. 12, 2008

(65) Prior Publication Data

US 2009/0126455 A1     May 21, 2009

(30) Foreign Application Priority Data

Nov. 20, 2007   (GB)   ................... 0722721.8

(51) Int. Cl.
*G01N 3/30*   (2006.01)
(52) U.S. Cl. ..................................... 73/12.11
(58) Field of Classification Search ................ 73/12.04, 73/12.11, 12.9, 12.06, 12.12, 12.13, 12.78
See application file for complete search history.

(56) References Cited

U.S. PATENT DOCUMENTS

2007/0125152 A1   6/2007   Brankov
2007/0220950 A1   9/2007   Goyal

FOREIGN PATENT DOCUMENTS

CH   SU 1108347 A   8/1984

*Primary Examiner*—Jewel Thompson
(74) *Attorney, Agent, or Firm*—Oliff & Berridge, PLC

(57) ABSTRACT

With regard to components it is necessary to test specimens of materials in order to determine acceptability for objective component performance. Previously such testing generally involved fixing and clamping of the test specimen which produced artificial stressing conditions. By providing a specimen component typically in the form of an elongate member which is suspended between mounting ends a combination is provided which has inertia. In such circumstances when a projectile impacts upon the elongate member that elongate member flexes and deforms and this deformation can be monitored for testing purposes. The projectile is arranged to have a relatively facile compliant nature upon impact with the component such that there is no local stressing of the component whilst suspending the mounting ends substantially avoids clamp resilience distorting objective or realistic stressing conditions.

15 Claims, 2 Drawing Sheets

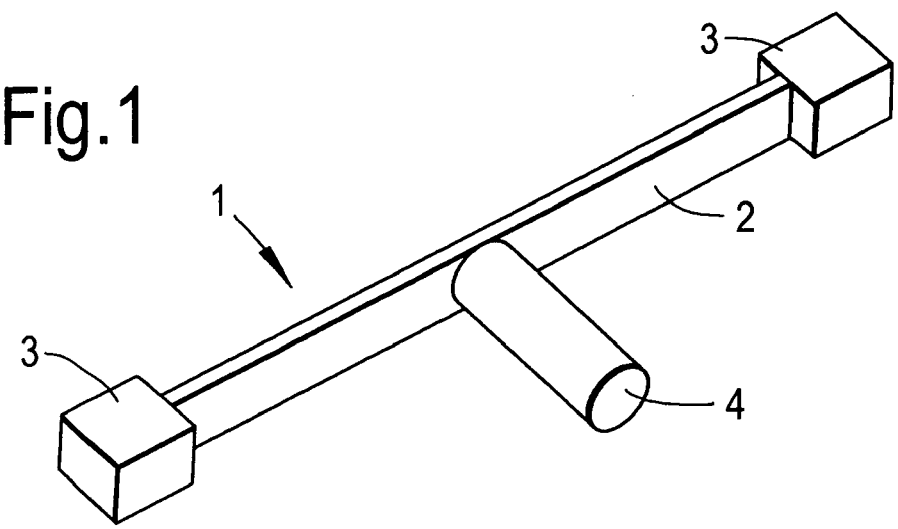
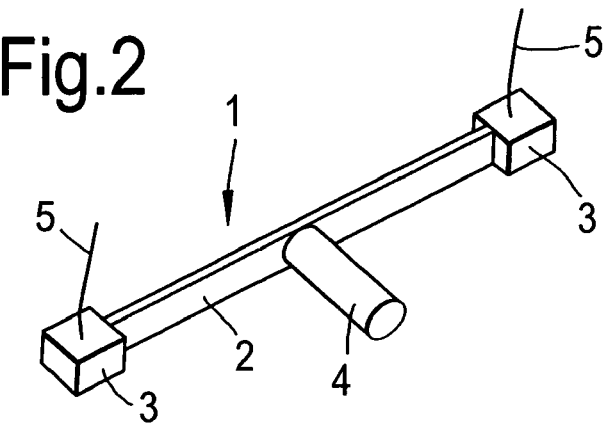
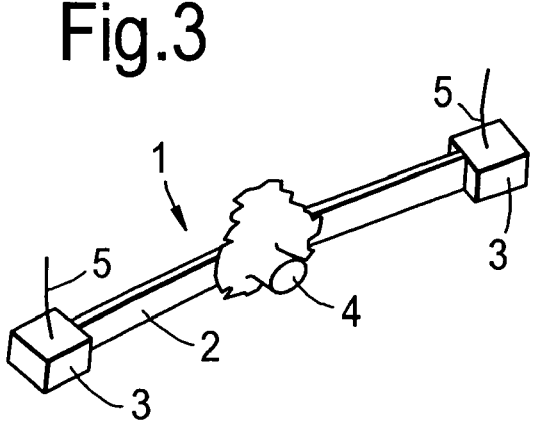
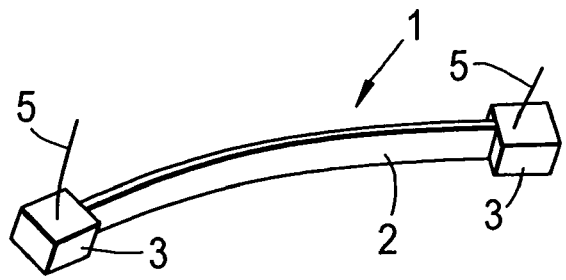

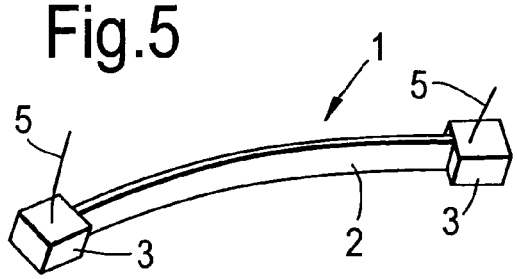
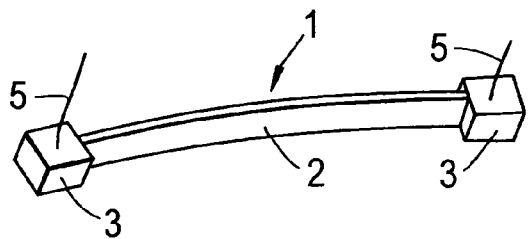
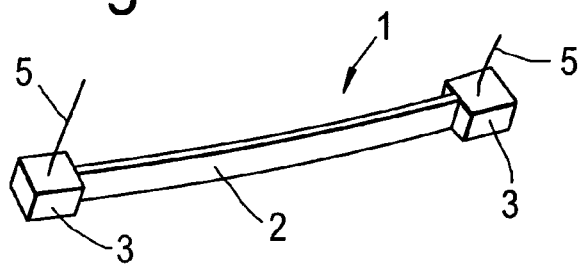
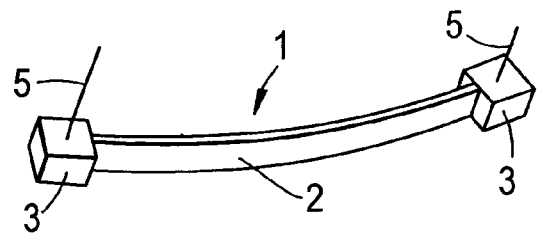
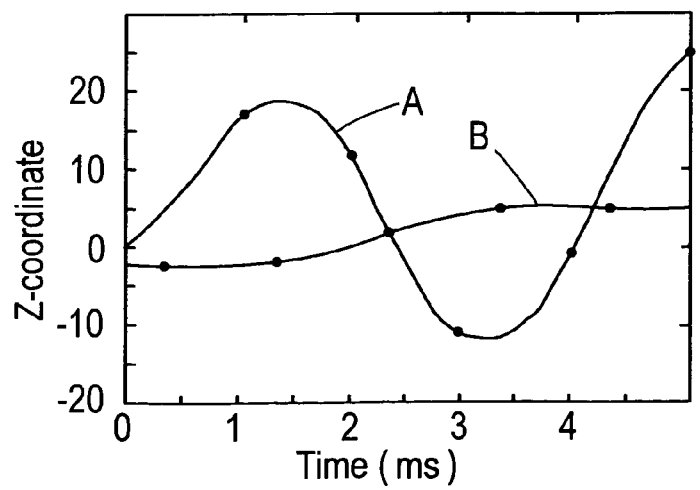

TEST APPARATUS AND METHOD OF TESTING

This application claim priority to Great Britain Patent Application No. 0722721.8, filed on Nov. 20, 2007, the entire disclosure of which is hereby incorporated by reference in its entirety.

BACKGROUND

The present invention relates to test apparatus and methods of testing components such as blades used in gas turbine engines and furthermore such components made from composite materials, laminated metals and having joints secured with adhesive.

Components can be made from a large range of materials and clearly must be tested in order to ensure physical parameters as well as operational capabilities are achieved. There are particular problems with regard to testing of composite materials as outlined below. It will also be understood it is desirable to test laminated metals such as glass/aluminium, aramid/aluminium and titanium/graphite combinations as well as components with adhesive joints.

Previously there have been a number of standard impact test methods including three-point beam bending, impacts on a plate and other methodology with regard to testing components or exemplary samples of component materials for desired performance.

SUMMARY

Unfortunately, previous test methods do not create realistic or practical stress states within a component particularly with respect to composite materials. Furthermore it is difficult to adequately model existing test methods or extrapolate responses to practical components. Typically prior test methods have used a specimen of the material from which the component is to be formed. In such circumstances for safety critical installations at least it has been known to create the correct stressing state by producing a test component itself which is then specifically tested as appropriate. Such an approach is complex and prohibitively expensive for speculative research, initial material selection and model evaluation. It would be advantageous to be able to at least initially test appropriate materials for members more accurately prior to specific forming of components for testing.

In accordance with the present invention, there is provided an test apparatus for components and a method of testing components as set out in the claims.

BRIEF DESCRIPTION OF THE DRAWINGS

An embodiment of the invention will now be described by way of example and with reference to the accompanying drawings in which:—

FIG. 1 is a schematic illustration of a test apparatus in accordance with a first aspect of the invention;

FIG. 2 is a schematic perspective view of a test arrangement in accordance with a first aspect of the invention prior to impact;

FIG. 3 is a schematic illustration of the apparatus as depicted in FIG. 2 under impact;

FIG. 4 is a schematic illustration of the apparatus as depicted in FIG. 2 and FIG. 3 subsequent to departure of an impact projectile;

FIG. 5 is a schematic illustration of the apparatus as depicted in FIGS. 2 to 4 and showing continuing bending under impact subsequent to projectile departure;

FIG. 6 is a schematic illustration of the apparatus as depicted in FIGS. 2 to 5 during initial reverse bending in response to the impact load;

FIG. 7 is a schematic illustration of the apparatus as depicted in FIGS. 2 to 6 showing continuing response bending;

FIG. 8 is a schematic illustration of the apparatus as depicted in FIGS. 2 to 7 at the end of response bending; and, FIG. 9 is a graphic illustration of monitored deflection response for an apparatus in accordance with a first aspect of the present invention.

DETAILED DESCRIPTION OF EMBODIMENTS

As indicated above testing of components such as elongate members is generally a question of applying test loadings up to expected practical impact loadings during a test methodology. In such circumstances providing a stress field of varying conditions in a composite panel that is representative of a soft body impact loading on a rotating aerofoil or similar elongate member would be desirable. In such circumstances achieving loading and deflections to achieve a superimposition of threshold and pressure loading upon a composite specimen and which allows reverse bending of the specimen would be advantageous. In such circumstances impacts would effectively be upon a fixed displacement type loading irrespective of specimen mounting stiffness.

In the above circumstances it will be appreciated that the resultant stress state is desirably at a representative level of bending stress in the plane of the component in the form of an elongate member or plate or other configuration such as a beam, box section or curved element as a test specimen and provides shear stress in the form of interlaminar stress. In such circumstances by appropriate choice of testing regime stress loading will be representative of practical conditions for the component. By such an approach it will be possible to model stressing of the component using finite element analysis as the boundary conditions will be more easily described. Such analysis will be significantly easier than with regard to prior clamped restraint type testing methodology and apparatus.

Ideally, methods of presenting the component as a test specimen should avoid localised stresses which may result in unrepresentative failure of the specimen. It will also be understood that test methodology in apparatus should generally be simple and cheap and able to provide several tests in an acceptable period of time. Furthermore, elongate members used as test components or specimens in the apparatus should also be relatively easy to produce and cheap to manufacture. As indicated the test components can be elongate, square panels, beams or box sections provided they give the necessary representation form.

The test apparatus and method provided by the invention is particularly adapted to testing components in the form of elongate members as specimens. The components are typically formed from composite materials but may also be made of laminated metals or jointed components. FIG. 1 provides a schematic illustration of a test apparatus 1 in accordance with a first aspect of the present invention. The apparatus 1 in use comprises a component 2 securely associated with end mountings 3. The component 2 as indicated is typically a composite material and extends into slots or other couplings within the mountings 3. The mountings 3 are generally heavy features in order to combine with the component 2 in order to define inertia for the apparatus 1 in a test mode. Typically, each mounting end 3 will have a mass in the order of 0.3 to 3 kg.

The component as indicated generally is an elongate member which extends between the mounting ends 3 and will have a set test size. This size may be in the order 200 mm long by 20 mm wide by 3 mm in depth but it will be appreciated that the size of the elongate member 2 may be varied within test ranges in order to appropriately test the elongate member 2 as a specimen. As with any test apparatus or test method regime, the elongate member 2 may be specifically configured to make desired specific analytical testing or a like for like standard elongate member 2 dimensions specified for comparing materials from which the respective elongate members are formed. In such circumstances the end members 3 may be matched with the elongate member 2 in order to achieve the desired inertia combination for comparison or otherwise.

The mounting ends 3 are suspended such that as indicated the inertia of these ends 3 along with the component 2 is utilised with respect to an impact provided by a projectile 4 arranged to impact on the elongate member 2. Typically this impact is central along the component 2. The projectile 4 has a relatively facile compliance relationship under impact with the elongate member 2. Such as a compliant relationship may be preferably achieved by having a soft projectile impacting upon a harder component or vice versa with a harder projectile impacting on a flexible soft component structure. In such circumstances the projectile 4 will deform and typically disintegrate, disperse or otherwise comply once a high impact load has been applied to the component 2. The projectile 4 is typically a cylindrical shape although other shapes could be utilised. In order to be relatively facile in compliance under impact with the elongate member 2 the projectile 4 would typically be formed from gelatine or a similar material such as an uncured foam, gel, or a membrane encapsulating a fluid or gel or cellular metal or cellular polymer etc. Furthermore, the projectile may be made up of pebbles or run-away gravel which applies the initial high pressure pulse before dispersion. As indicated these specific test conditions are provided for a particular component or standardised test conditions and parameters may be specified for component comparison. Furthermore, impacts upon the test component are generally perpendicular although alternative angles may be useful to investigate other failure modes.

As indicated above the end mountings 3 are typically suspended. Such suspension is advantageously achieved through vertical cables as depicted in FIG. 2 which extend down to present the mounting ends 3 and the component 2. The cables 5 will generally as indicated suspend the component 2 in a frame or cradle such that the projectile 4 is appropriately presented to the component 2. As can be seen in FIG. 2 the projectile 4 has a typical cylindrical shape although other shapes could be used. The depiction in FIG. 2 is just prior to impact by the projectile 4 upon the component 2 and therefore it will be seen that the component 2 is substantially straight or has the shape dictated by the test methodology. The projectile 4 as indicated is compliant but defines a mass which will be propelled towards the component 2. Typically the projectile 4 will be propelled at around a 100 meters per second in order to generate appropriate impact load upon the component 2. As indicated above impact will normally be perpendicular and initially generate a high pressure load pulse. This load pulse then decays to a stabilised pressure as the projectile flows due to elasticity or disintegrates. The projectile 4 as indicated will be relatively facile and compliant upon impact with component 2. As the projectile 4 has mass typically in the order of 10 to 30 grams and preferably around 20 grams deflection and distortion of the component 2 will occur against the suspended inertia defined by the end mountings 3 and component 2.

The facile impact created by the gelatine or similar nature of the material from which the projectile 4 is formed results in "soft" contact with the component 2. This induces interlaminar stress within the component 2 without unrepresentative localised damage which may occur if a large hard impact projectile is used unless the test component 2 is soft and compliant and gives the deserved impact relationship. FIG. 3 illustrates the apparatus 1 in mid impact. Thus, as can be seen the projectile 4 has become compliant and spread upon impact with component 2. This causes a three-point bend operation resulting in a load upon the component 2. Restraint is created by the inertia of the combination of the ends 3 and the elongate member 2. This allows easy modelling of the loading upon the component 2 as it avoids localised bending stress at the point of contact by the projectile 4. The mass of the combination of the component 2 and the ends 3 results in deflection being dominated by the inertia of the combination rather than the stiffness of the component specimen which was a problem with prior fixed or clamped arrangements where the test specimen was securely fixed and clamped. As indicated the mass of the combination of the component 2 and the ends 3 dominates in the flexure response hence the combination will generally move very little in space. It will be appreciated that the matching of the projectile 4 mass with the inertia mass of the combination of the ends 3 and component 2 should be carefully chosen such that as indicated there is very little displacement in space. It will be understood that the suspension mechanism depends upon such stabilised displacement and allows the use of a cable support method. If there was significant displacement this would introduce restraint possibly creating erroneous results. Ideally the cables 5 will simply hang during an impact regime with flexing and deflection of the component 2, accommodating the impact load provided by the projectile 4.

The cables 5 will be suspended in order to present the ends 3 and component 2 to minimise rotational inertia and ensure minimal localised bending stress where the specimen is clamped in the ends 3.

In the above circumstances it will be appreciated that the strain rates achieved are typically due to the dimensions of the component 2 and the rate of impact loading provided by the projectile 4.

In the above circumstances a method is provided in which a component 2 is effectively loaded and coupled to ends 3 which are suspended upon the cables 5. The elongate member 2 is then subject to an impact load from a soft projectile 4 and deflection of the component 2 monitored against time to give a characteristic response.

It will be understood that dependent upon the degree of damage sustained typically some impact energy will be stored within the component 2 and consequently the component 2 will respond by reverse flexural bending and loading. FIG. 4 through to FIG. 8 illustrate this deformation response of the component 2.

In FIG. 4 the apparatus 1 is depicted just after the projectile disintegrates subsequent to full impact with the component 2. In such circumstances it can be seen the component 2 has at least partially deformed and bent.

In FIG. 5 the apparatus 1 subsequent to the configuration as depicted in FIG. 4 is shown in schematic form. As can be seen the component 2 has continued to bend as a result of impact loading and inertia effects in the apparatus 1. The degree and maximum extent of bending of the component 2 will be a characteristic of the material and dimensions of the component 2.

FIG. 6 illustrates the apparatus 1 showing initial reverse bending of the component 2 as a result of stored "elastic" strain energy within the component 2 released by the suspension of the ends 3 upon the cables 5.

FIG. 7 illustrates further reverse bending of the component 2 as result of elastic energy within the component 2.

FIG. 8 illustrates the furthest extent of reverse bending as a result of elastic energy within the component 2 built up as a result of impact with the projectile 4 (not shown).

It will be noted through the deformation stages depicted from FIGS. 2 to FIG. 8 that the component 2 is deflected over time by the impact loads presented by the projectile 4. FIG. 9 provides a graphic illustration of deflection in respect of an aperture. As can be seen a curve A illustrates deflection by a component and curve B deflection by the mounting ends 3. These deflections A, B are taken over a time period in which the component 2 flexes. This time period for illustration purposes is 5 milliseconds. It will be noted that the deflection of the component is symptomatic of the particular materials and dimensions of the component 2. In such circumstances the curve A, B can be utilised for comparison with other sample components for analytical and design purposes.

The invention provides an apparatus and a method for testing specimen components. As indicated this testing may be relative to a known set of parameters achieved empirically or through finite element impact modelling for a desire operative performance. Alternatively, a deflection response curve as depicted in FIG. 9 may be determined for an acceptable performance by a component to be tested through a representative specimen.

The invention is particularly useful with regard to components formed from composite materials. In such circumstances these composite materials will generally comprise a hybrid of more than one material combined within a laminate or fibre reinforcement within the material. Specifically, the invention is applicable to testing carbon fibre reinforced polymer components presented in the form of elongate members between the end mountings.

The invention addresses fundamental problems with regard to testing of laminate materials. In such circumstances the method and apparatus of the present invention can provide an accurate reconstruction of the stress state and damage within a real component by achieving a desired inertia mass combination between the mountings ends 3 and representative component 2 in relation to the dimensions of the component such as length, width and thickness. In such circumstances a more realistic response from the material from which the component is formed is achieved in order to adapt and formulate design objectives. Such advantages may have particular applicability with regard to fan blade development within gas turbine engines. The present method and apparatus allows cheap, repeatable, easily understood, straight forward and more realistic modelling of impact load stressing upon components to be provided without the necessity of resorting to producing actual real components designed for destructive testing.

Modifications and alterations to the invention will be understood by those skilled in the art. Thus, generally the specimen component is typically in the form of an elongate member and will be substantially flat in its original suspended state prior to impact. However, it will also be understood that components which are initially bent or curved or kinked may also be tested. Furthermore, the impact site for the projectile may be substantially central or adjusted along the length of the component to match expected operational stressing upon the component. Although suspension upon cables hanging vertically down has particular advantages it will also be understood that other forms of suspension may be appropriate including where possible suspension upon gas or air jets or other fluids as it will be understood that ideally the mounting ends provide inertia in association with the component such that positional site retention is achieved whilst impact energy is principally absorbed through flexing and deformation of the component itself.

I claim:

1. A test apparatus for a component, the apparatus comprising:
   an end mounting for each end of the component, each end mounting suspended in use; and
   a projectile having a relatively facile compliance under impact with the component in use to cause distortion of the component.

2. An apparatus as claimed in claim 1 where the projectile is formed from gelatine or similar material.

3. An apparatus as claimed in claim 1 wherein the projectile has a mass in the order of 10 to 30 grams.

4. An apparatus as claimed in claim 1 wherein the projectile is projected at a velocity in the order of 100 meters per second.

5. An apparatus as claimed in claim 1 wherein the projectile produces a pressure pulse followed by stabilised flow under impact with the component in use.

6. A test apparatus for a component the apparatus comprising:
   an end mounting for each end of the component, each end mounting suspended in use; and
   a projectile having a relatively facile compliance under impact with the component in use to cause distortion of the component, wherein the end mountings are suspended upon cables.

7. An apparatus as claimed in claim 1 wherein the end mountings are matched to the component to provide a desired value for inertia.

8. An apparatus as claimed in claim 1 wherein the end mountings have a mass in the order of 0.3-3 kg.

9. A method of testing a component, the method comprising:
   presenting the component between end mountings;
   suspending the end mountings with the component between;
   causing an impact by a projectile having relatively facile compliance under impact with the component to cause distortion of the component against inertia defined by the component and the end mountings; and
   monitoring the distortion of the component.

10. A method as claimed in claim 9 wherein the projectile is formed from a gelatine or similar material.

11. A method as claimed in claim 9 wherein the projectile has a mass in the order of 10 to 30 grams.

12. A method as claimed in claim 9 wherein the projectile is projected at a velocity in the order of 100 meters per second towards the component.

13. A method as claimed in claim 9 wherein the projectile causes a pressure pulse followed by stabilised flow under impact with the component in use.

14. A method as claimed in claim 9 wherein the end mountings are matched to the component to provide a desired value for inertia.

15. A method as claimed in claim 9 wherein the end mountings have a mass in the order of 0.3-3 kg.

* * * * *